US009233516B2

(12) United States Patent
Kusin et al.

(10) Patent No.: US 9,233,516 B2
(45) Date of Patent: Jan. 12, 2016

(54) CLOTHING WIPE (75) Inventors: Ben Kusin, Dallas, TX (US); Charles C. Steward, Midland Park, NJ (US); Ronald C. Griepenburg, Oradel, NJ (US); Edgardo Guce, New Milford, NJ (US)

(73) Assignee: Kusin & Kusin, Ltd., Dallas, TX (US)

( * ) Notice: Subject to any disclaimer, the term of this patent is extended or adjusted under 35 U.S.C. 154(b) by 441 days.

(21) Appl. No.: 13/606,827

(22) Filed: Sep. 7, 2012

(65) Prior Publication Data
US 2013/0007973 A1 Jan. 10, 2013

Related U.S. Application Data (63) Continuation-in-part of application No. 11/386,425, filed on Mar. 22, 2006, now abandoned.

(51) Int. Cl.
*A47L 13/19* (2006.01)
*A47L 25/08* (2006.01)
*D06B 1/00* (2006.01)
*B31D 1/00* (2006.01)

(52) U.S. Cl.
CPC . *B31D 1/00* (2013.01); *A47L 13/19* (2013.01); *A47L 25/08* (2013.01); *D06B 1/00* (2013.01)

(58) Field of Classification Search
CPC .......... A47L 13/19; A47L 25/08; C11D 3/00; D06B 1/00
See application file for complete search history.

(56) References Cited

U.S. PATENT DOCUMENTS

| 1,654,161 | A |   | 12/1927 | Diaz et al. |
| 2,621,784 | A |   | 12/1952 | Van Boytham |
| 2,790,982 | A |   | 5/1957 | Schneider |
| 3,608,708 | A | * | 9/1971 | Storandt ........................ 206/361 |
| 3,638,789 | A |   | 2/1972 | Tuszewski |
| 3,775,014 | A |   | 11/1973 | Rosborne |
| 5,227,226 | A | * | 7/1993 | Rzasa ........................... 428/219 |
| 5,584,163 | A |   | 12/1996 | Storandt |
| 5,650,143 | A |   | 7/1997 | Bergmann et al. |
| 5,802,655 | A | * | 9/1998 | Denton ........................ 15/104.93 |
| 5,830,487 | A |   | 11/1998 | Klofta et al. |

(Continued)

FOREIGN PATENT DOCUMENTS

WO 2007/111927 A2 10/2007
WO 2009/111365 A2 9/2009

OTHER PUBLICATIONS

Hartz® "Quick Wipes™ Value Pack," product webpage, 1 page, Copyright © 2013 The Hartz Mountain Corporation, www.hartz.com/Hartz_Products/Dog_Products.

(Continued)

*Primary Examiner* — Randall Chin
(74) *Attorney, Agent, or Firm* — Whitaker Chalk Swindle & Schwartz PLLC; Stephen S. Mosher (57) ABSTRACT

A clothing wipe includes an applicator having a novel odor neutralizing formulation deposited on one layer that is bonded to another layer to form a finger mitt. The applicator is removed from a pouch and rubbed against a person's clothing that may have accumulated a variety of smoke, food, and other odors during an outing. The odors clinging to the clothing are neutralized by contact with the odor neutralizing formulation. The applicator is stored in the pouch when not in use. A method of fabricating the clothing wipe in a web process is disclosed.

21 Claims, 7 Drawing Sheets

(56) References Cited

U.S. PATENT DOCUMENTS

| | | | |
|---|---|---|---|
| 5,904,151 | A | 5/1999 | Gueret |
| 6,238,682 | B1 | 5/2001 | Klofta et al. |
| 6,250,829 | B1 | 6/2001 | Brower et al. |
| 6,481,443 | B1 | 11/2002 | Moore-Johnson et al. |
| 6,726,386 | B1 | 4/2004 | Gruenbacher et al. |
| 6,756,520 | B1 | 6/2004 | Krzysik et al. |
| 6,811,338 | B1 | 11/2004 | Gruenbacher et al. |
| 6,821,940 | B2 | 11/2004 | Bullock et al. |
| 6,951,421 | B2 | 10/2005 | Crunkleton et al. |
| 6,991,842 | B2 | 1/2006 | Hurwitz |
| 7,122,238 | B2 * | 10/2006 | Macedo .................. 428/136 |
| 7,169,400 | B2 | 1/2007 | Luu et al. |
| 7,235,250 | B2 | 6/2007 | Padlo et al. |
| 7,250,392 | B1 | 7/2007 | Leonard et al. |
| 7,346,955 | B2 | 3/2008 | De Laforcade |
| 7,361,361 | B2 | 4/2008 | Luu et al. |
| 7,482,021 | B1 | 1/2009 | Tison et al. |
| 7,594,344 | B2 | 9/2009 | Mizrahi |
| 7,748,140 | B2 | 7/2010 | Mizrahi |
| 7,845,360 | B2 | 12/2010 | Walters et al. |
| 8,158,689 | B2 | 4/2012 | Baker et al. |
| 8,168,280 | B2 | 5/2012 | Thiele |
| 8,232,276 | B2 | 7/2012 | Burnett et al. |
| 2002/0013108 | A1 | 1/2002 | Dobler |
| 2002/0124335 | A1 | 9/2002 | Franko, Sr. |
| 2003/0009138 | A1 | 1/2003 | Freeman et al. |
| 2003/0037797 | A1 | 2/2003 | Fang |
| 2004/0237235 | A1 | 12/2004 | Visioli et al. |
| 2005/0120497 | A1 | 6/2005 | Lynde et al. |
| 2005/0220374 | A1 | 10/2005 | Thomas et al. |
| 2006/0005333 | A1 | 1/2006 | Catalfamo et al. |
| 2006/0225233 | A1 | 10/2006 | McKay |
| 2007/0220692 | A1 | 9/2007 | Kusin |
| 2007/0227044 | A1 | 10/2007 | Maxson |
| 2010/0058551 | A1 * | 3/2010 | McDowell .................. 15/210.1 |
| 2012/0100195 | A1 | 4/2012 | Sainz et al. |

OTHER PUBLICATIONS

Photocopies of wipe products available copyright 2005 from the Clorox Co. and Armor All/STP Products Co., 1 page.

Armor All webpage; Car Stain Remover by Armor All (registered); To-Go Cleaning Wipes; 1 page; www.armorall.com; copyright 2012.

Clorox (registered) webpages; Disinfecting Wipes for Multi-Surface Cleaning: 3 pages; www.clorox.com; Nov. 2012.

"Single Chamber Two Finger Transmit" (TM); Padtech The Science of Application product webpage; 1 page; copyright 2012; Flemington, New Jersey http://padtech.net/singleChamber_2finger.htm.

"Dual Chamber 3 Finger Transmit" (TM) Padtech The Science of Application product webpage; 1 page; copyright 2010; Flemington, New Jersey http://padtech.net/dualChamber_3finger.htm.

* cited by examiner

CLOTHING WIPE

RELATED APPLICATIONS

The present Application is a Continuation-In-Part of U.S. patent application Ser. No. 11/386,425 filed Mar. 22, 2006 by Ben Kusin and entitled ODOR NEUTRALIZATION APPARATUS AND METHOD.

FIELD OF THE INVENTION

The present invention generally relates to neutralizing unpleasant odors and, more particularly, to apparatus and a method for neutralizing unpleasant odors that may cling to the surface of a person's clothing and refreshing the scent of the clothing.

BACKGROUND OF THE INVENTION

Dining out, attending concerts or dance performances, going to the theatre or to movies, going to parties, dances and celebrations, going to night clubs and other entertainment venues, or just hanging out with friends are some of the activities people engage in during their free time. Generally, in preparing to participate in these activities, people take great pains to look their best and to present themselves in the best possible light. Personal grooming aids and products are often employed, most of which are scented, in an effort to appear attractive. Perfumes and scented grooming products are used to enhance the effects, particularly among persons interested in attracting other persons of the opposite sex, for example.

Unfortunately, the scented effects tend to diminish rapidly, reducing the intended effect of the personal grooming efforts. Further, many of the venues for the above activities include exposure to a wide variety of odors. These odors typically originate from food and beverages in restaurants, from smoke in restaurants, bars, night clubs, etc., from the perspiration of the persons themselves and other patrons, and from other substances that may be encountered during an evening's entertainment. Many of these odors are unpleasant or become more so with the passage of time. Such odors are readily absorbed by a person's clothing or hair, and are carried with the person for the rest of the evening. Thus, not only are the original scents diminished through the natural evaporation and deterioration that occurs, but they are often overwhelmed or masked by the many odors in the surroundings. These circumstances may be especially worrisome to people in a dating situation, especially as the evening wears on and the persons anticipate extending the evening or just wish to freshen themselves before proceeding with the remainder of the evening's activities, one's next appointment, etc. Other circumstances where the need to refresh one's clothing or hair may arise include following a long or arduous meeting, working out in a gym, a long walk between offices, playing with pets, and the like.

Conventional remedies include perfume or perfumed products such as cologne applied to a person's skin or clothing, typically provided in a spray container or a bottle. Other similar products may be applied by hand. Further, it is known that certain products, such as dryer sheets for use in clothes dryers, have sometimes been used in an effort to absorb the unpleasant odors from a person's clothing or hair, but generally with limited success. Further, such dispensing devices as traditionally used for perfume or cologne are not readily available with odor neutralizing capabilities adapted to neutralizing the odors accumulated on a person's clothing. Moreover, the use of paper or fabric odor absorbing devices has heretofore failed to provide more than limited usefulness.

It is known or has been observed that certain paper or fabric products, such as the Bounce® dryer sheets and Swiffer® floor mop products manufactured and distributed by the Proctor & Gamble Corporation for the laundry and floor cleaning markets respectively, and which may respectively contain anti-static or scented compounds or cleaning agents, have certain properties that might suggest possible applications in this field of odor neutralization of clothing. However, the available configuration of these articles is not appropriate or well suited to the application of neutralizing the odors absorbed by a person's clothing in a night club or restaurant venue. The Bounce® dryer sheets and the Swiffer® mop refills are loose sheets of fabric. They are not conveniently packaged for a person's pocket or purse, are not adapted to the particular use of odor neutralization of a person's clothing, and do not contain suitable substances for neutralizing odors absorbed into or clinging to a person's clothing or for refreshing originally applied perfumes or scents.

What is needed is an apparatus and a method of using the apparatus, which overcomes the disadvantages of the prior art devices and methods, that can serve both to eliminate or neutralize unpleasant odors that accumulate on a person's clothing during an evening's entertainment in a wide variety of venues, and to refresh or restore the original scent or replace it with an alternative scent.

SUMMARY OF THE INVENTION

Accordingly there is disclosed a personal care apparatus for neutralizing odors on a person's clothing. The apparatus comprises a hand-held applicator formed of a first layer and a second layer bonded together along mutual edges thereof except along a portion of the mutual edges thereby forming a pocket or sleeve; an odor neutralizing formulation uniformly deposited on an outer side of the first layer of the applicator, wherein the formulation includes a base component and a neutralizer component; the base component includes approximately 86% polyethylene glycol ester and 10% glycerin and the neutralizer component includes a fragrance mixture formed of essential oils and one or more aroma compounds combined in predetermined proportions; and a pouch for enclosing the applicator when not in use, the pouch formed of a flexible packaging film and having a reusable closure mechanism disposed along one side thereof.

In another embodiment, a method for fabricating a clothing wipe is provided, comprising the steps of forming a first layer of an applicator in a first branch of a web process including uniformly depositing an odor neutralizing formulation on an outer surface of said first layer; forming a second layer of said applicator in a second branch of a web process including imprinting said second layer with indicia followed by merging said first and second web process branches in a step for aligning said first and second layers of said applicator for cutting, trimming and bonding operations; and forming and imprinting a storage pouch for said applicator from flexible packaging film in a third web process followed by merging said third web process branch with said combined first and second web process branches in a step to insert said applicator in said storage pouch.

In another aspect of the method for fabricating a clothing wipe, the step of formulating the odor neutralizing formulation includes the steps of combining a fragrance mixture in a predetermined proportion to provide a fragrance component having a "clean linen" aroma; and combining the fragrance component with a base component including a mixture of a polyethylene glycol ester and glycerin. In another aspect, the polyethylene glycol ester is combined with the glycerin in respective proportions of 86% and 10% of the odor neutralizing formulation.

In another embodiment, there is disclosed an apparatus for neutralizing odors in clothing, comprising an applicator for applying a neutralizing substance to a person's clothing, the applicator including a carrier layer having a generally rectangular shape defined by a perimeter thereof and impregnated with the neutralizing substance, and a substrate layer having generally the same shape as the carrier layer and bonded to the carrier layer around all but a select portion of the perimeter of the carrier layer to form a finger pocket for manipulating the applicator. In an alternate embodiment, an activating mechanism or protective sleeve associated with the applicator may be provided for releasing the neutralizing substance from the carrier layer.

In another aspect of the invention, a method is disclosed comprising the steps of providing an odor-neutralizing applicator having a carrier layer impregnated with an odor neutralizing substance and adapted to be slipped over the person's fingertips of one hand; slipping the applicator over the fingertips of the person's hand; and manipulating the applicator against the person's clothing to neutralize the odors in the person's clothing. In an alternate embodiment the method includes the step of activating the carrier layer of the applicator to release the odor neutralizing substance onto the person's clothing.

DETAILED DESCRIPTION OF THE INVENTION

Figure 1:
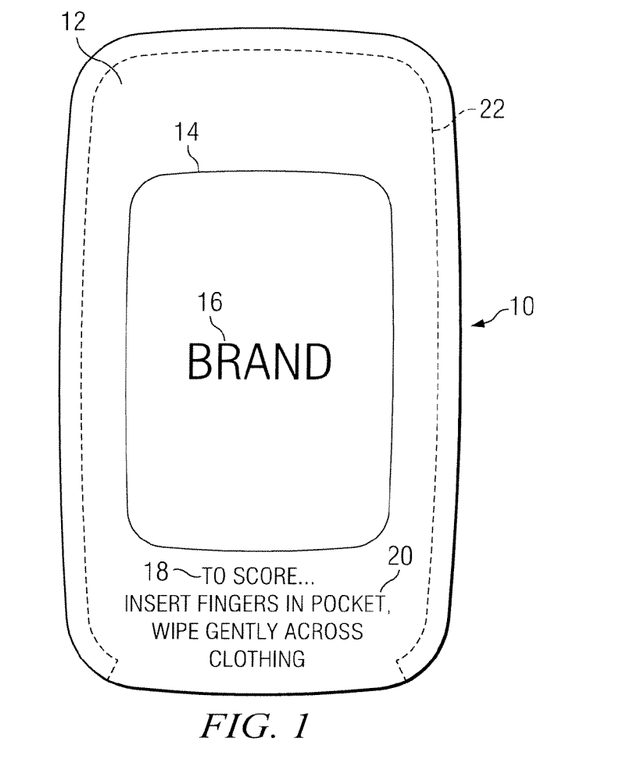
FIG. 1 illustrates a plan view of one embodiment of an apparatus for neutralizing odors on a person's clothing.

Referring to FIG. 1, there is illustrated a plan view of one embodiment of an apparatus for neutralizing odors on a person's clothing by refreshing the person's clothing through odor neutralization and new scent deposition. An applicator 10 includes a top layer 12, which may bear a brand indicia 14 including a brand 16, and, as one alternate embodiment, a textual indicia 18 including instructions 20 for using the applicator 10. In an alternative, wherein the top layer 12 includes only a brand indicia, textual indicia may be affixed to or printed upon the packaging for the applicator 10. A bonding region 22 is shown, indicating the location of a bond that is formed between the top layer 12 and other layers (not shown in FIG. 1) below the top layer 12. It will be observed, however, that the bonding region 22, between the edge of the applicator 10 and the dashed line, surrounds the perimeter of the applicator 10 around all of the perimeter except for one edge of the applicator 10. The edge of the applicator 10 that does not include a bond is selected so that a person's fingertips may be inserted between two of the layers, as will be explained.

The applicator 10 in its preferred embodiment is intended to be a compact device easily carried in a pocket or purse. Thus, its dimensions are determined accordingly to be slim and only slightly larger than a business card, for example. The applicator 10 in the illustrative embodiment shown in FIGS. 1, 2 and 3 may be approximately 3.75 inches long and approximately 3.00 inches wide. The top layer 12 may be a paper material bearing the indicia 14, 18, which may, for example, be printed or embossed thereon by conventional processes. In alternative embodiments, however, the dimensions and shape of the applicator 10 may of course be modified for other applications without departing from the concept illustrated in FIGS. 1, 2 and 3. In general, the shape may be any plane figure that is bounded by a closed perimeter, such as triangular, rectangular, circular, elliptical, oval or polygonal. The portion of the perimeter that is open, called the open space 28, to permit the users fingers to be inserted between a carrier layer 26 and a substrate layer 24 (See FIG. 2) in the manner of a finger min, may be located at any location along the perimeter of the applicator 10. In a preferred embodiment, the shape of the applicator 10 is generally rectangular with rounded corners, wherein the open space 28—an entry side for inserting the user's fingers—is located along one of the shorter sides of the applicator 10. Other embodiments may position the open space 28 along a longer side or a curved side.

Figure 2:
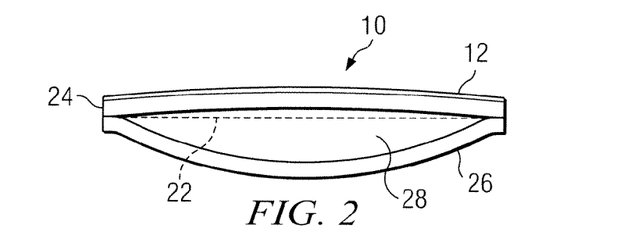
FIG. 2 illustrates an edgewise view of the embodiment of FIG. 1.

Referring to FIG. 2, there is illustrated an edgewise view of the applicator 10. The structure of the embodiment shown includes three layers of material, each with a distinct purpose. The top layer 12 has been described previously. It may be bonded fully to an intermediate substrate layer 24, which may be fabricated from a thin, generally flexible and substantially non-absorbent material that has some stiffness or resiliency to provide shape and "body" to the applicator 10. The purpose of the substrate layer 24 is to form a pocket in cooperation with the carrier layer 26 when the applicator 10 is prepared for use. Materials suited to this purpose include leather, synthetic, leather-like fabrics, heavy grade papers, and the like. The lower layer, the carrier layer 26, is preferably an absorbent layer of a non-woven fabric, such as may be formed of spun-bonded polyester fibers. This example, of which the fabric such as that used in the aforementioned dryer sheets is just one alternative, is illustrative only and a number of alternative fabric materials are feasible. The carrier layer 26 is preferably impregnated with an odor neutralizing substance to be described. In alternate embodiments, the carrier layer 26 may include pleasantly scented material such as perfume or cologne, either alone or in combination with the odor neutralizing substance.

The carrier layer 26 may be bonded to the substrate layer 24 around the perimeter of the substrate layer 24 except at the selected open space shown in FIG. 2. This open space is provided for the person using the applicator 10 to insert his or her fingertips into the pocket 28 between the carrier layer 26 and the substrate layer 24 for the purpose of manipulating the applicator 10 during use. The edge of the bonding region 22, represented by a dashed line (also indicated by reference number 22), is shown within the pocket 28 between the substrate 24 and carrier 26 layers. The dashed line 22, also shown in FIG. 1, may in one embodiment indicate one location of stitches for sewing the edges of the bonding region 22 together. The edges of the bonding region 22 may also be bonded using an adhesive, rivets, staples, clamps or crimped fasteners, or even be an integral part of both the substrate 24 and carrier 26 layers of the applicator 10. An example of the latter embodiment is provided when the substrate 24 and carrier 26 layers are formed of a single sheet of material that satisfies the requirements of both layers.

In some embodiments it is advantageous for the applicator 10 to be disposable; that is, it may be discarded when the odor neutralizing substance impregnated in the carrier layer 26 is exhausted. Thus, the materials used in the construction of the applicator 10 need not be particularly durable. On the other hand, it is further contemplated that other embodiments of the applicator 10 may be reusable. For example, an applicator 10 constructed of relatively durable materials and configured to be fitted with a replaceable carrier layer 26, may be provided. The latter embodiment might provide a marketing advantage in that the applicator may be provided at nominal cost with or without a package of refill carrier layers 26 (or, carrier sheets 26). A reusable applicator would include a bonding mechanism to enable removal of the carrier layer 26 for replacement by a fresh carrier layer 26.

Figure 3:
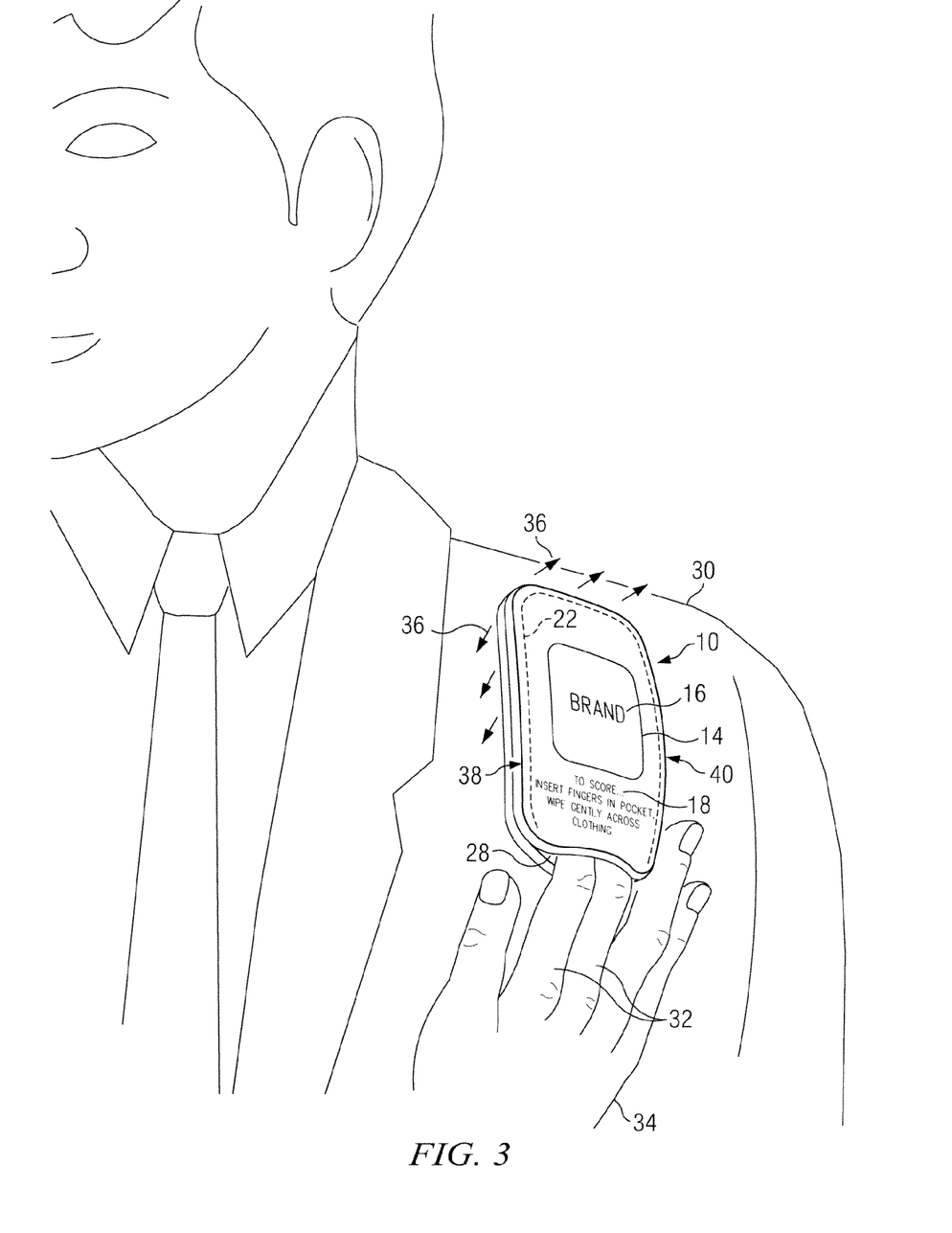
FIG. 3 illustrates a pictorial view of the use of the embodiment of FIG. 1.

Referring to FIG. 3, there is illustrated a pictorial view of the applicator 10 being used to apply the odor neutralizing substance to a person's clothing. The applicator 10 is shown being manipulated by a wiping action against the clothing 30 of a user, as indicated by the arrows 36. The user's fingertips 32 of his or her hand 34 are inserted into the pocket 28 between the substrate 24 and carrier 26 layers of the applicator 10. In a preferred embodiment, the pocket 28 in the applicator 10, when opposite sides (e.g., to the left and right of the applicator 10 as indicated by the triangular marks 38, 40 in FIG. 3) of the applicator 10 are squeezed slightly, opens wide enough to receive two fingertips 32 therein for manipulating the applicator 10. Once installed on the user's fingertips, his or her hand 34 is moved in a side-to-side motion 36, rubbing or wiping the lower surface portion (not visible in the figure, but will be readily understood) of the carrier layer 26. This action causes the release and transfer of the odor neutralizing substance from a portion of the carrier layer 26 to the surface of the user's clothing 30, as will be described further herein.

Continuing with FIG. 3, the odor neutralizing substance may, for example, be an activated charcoal material, impregnated into or formed into a fabric used to construct the carrier layer 26, that absorbs odor particles on contact with the carrier layer 26. In an alternative embodiment, a compound that combines with the chemicals in food odors and smoke, thereby causing them to be non-odorous, may be activated on contact with the person's clothing. In another alternative embodiment, a compound that volatilizes odorous substances on contact, causing them to disperse by evaporation may be used. Alternate embodiments may utilize a combination of these features in a single device to accomplish odor neutralization. For example, a device may combine the features of absorption and ionization to neutralize odors accumulating on the surface of clothing. Further, the odor neutralizing substance may be bound in microcapsules impregnated within the carrier layer, thus prevented from escaping until subjected to the pressure associated with the rubbing or wiping contact 36 against the user's clothing surface when the applicator 10 is being used. The odor neutralizing substance may additionally include a perfume or other scented agent. Alternatively, the perfume or scented agent may be separately impregnated into the carrier layer 26.

In one example, an activated charcoal material that is formed into a textile fabric having a microporous structure may be used in the carrier layer 26. The microporous structure provides a very large surface area presented to the odor-causing substances, effectively absorbing them from the person's clothing during use of the applicator 10. The activated charcoal textile material, developed in Britain for its filtering properties, is further disclosed in U.S. Pat. No. 6,313,371 issued to Conant et al.

The following detailed description describes several alternative and preferred embodiments with reference to FIGS. 4 through 10.

In one preferred embodiment to be described with reference to FIGS. 4, 5, 6, and 7, the odor neutralizing substance may include a formulation comprising a base component and an organic odor neutralizer component combined in predetermined proportions. In the illustrated example, the base component may comprise a mixture of a polyethylene glycol ester and glycerin, in approximate respective percentages of 86% and 10%. The polyethylene glycol (PEG) ester, a soft, colorless material is provided as a base component—a carrier—that provides sufficient body to the formulation to hold the odor neutralizer component in a solid matrix. When the clothing wipe device is rubbed along the surface of the clothing, a thin film of the carrier or base, with the neutralizer combined therewith, is deposited on the surface of the clothing. This film leaves no stain and may be removed when the clothing is washed. The glycerin is soluble in the base and provides a softening effect on the base, while slowing the release of the fragrance component of the odor neutralizer to be described. The glycerin is also washable and leaves no stain, and has a low vapor pressure so that the stability and shelf life of the device are enhanced.

The organic odor neutralizer component may comprise a fragrance component or mixture or composition. This component comprises approximately 4% of the total odor neutralizing formulation. Fragrance mixtures are well known and are available in a wide variety of formulations or types, for neutralizing a wide variety of odors. Some of the available types include: a masking agent, a solvent, an absorbant, an encapsulant, and a spray dry fragrance. In the present invention, one class of fragrance compositions or mixtures has been found particularly suitable for counteracting or neutralizing odors on clothing or a person's hair, for example. Such a fragrance mixture is a blend of several constituents that is formulated to present—i.e., leave behind on the user's clothing—a "clean linen" aroma or scent. In the illustrated embodiment, the constituents of the fragrance mixture may include chemicals of an aromatic or aliphatic nature such as aldehydes, ketones, alcohols, esters, and materials containing oxygen, nitrogen or sulphur. The fragrance mixture preferably comprises approximately 4% of the total odor neutralizing formulation. However, due to the subjective nature of the sense experience, this proportion may be varied by experimenting with the proportions to be mixed. For example, the test may begin by varying the ingredients in greater or lesser proportion until a preferred proportion is determined for a particular application.

In regard to the proportions of the three principal ingredients of the odor neutralizing formulation described above in specific percentages, it is important to point out that these are percent values arrived at for one embodiment of the illustrated clothing wipe. The clothing wipe may be configured for a variety of specific applications depending on the market for such variations. Accordingly, the proportions of the these ingredients may be varied to suit particular formulations to meet a specific target market segment. In general, the proportion of the polyethylene glycol ester may range from 80% to 90%, the glycerin (or an acceptable substitute) may range from 6% to 16%, and the fragrance mixture may range from 0.5% to 10%. Potential market segments may be gender-specific or unisex, or directed to particular kinds of activities such as indoor or outdoor, social or business or recreation, etc. Other applications may include clothing wipes that are formulated as insect repellants or other ancillary uses besides refreshing the scent or odors present on a person's clothing or hair. Such applications may include ingredients that are combined in proportions that differ substantially from those set forth herein. For example, a wipe having an insect repellant substance may include 15% to 30% repellant chemical in combination with a base component of 70% to 85% and a fragrance mixture of a few percent, for example. Other applications may include wipes having formulations adapted to a person's skin surfaces. Such applications may include ingredient formulations based on other types of ingredients in other proportions, etc. Thus, the clothing wipe described herein is only one example of a versatile delivery system for scented or other chemical formulations configured for a wide variety of personal care products.

In use, as described herein below, the rubbing action that occurs when the clothing wipe device is brought into contact with the user's clothing or hair and deposits the odor neutralizing formulation or substance in proportion to the degree of force used and the length of path or amount of time expended as the device is rubbed across the surface of the clothing. This provides a convenient way to regulate the amount of odor neutralizing formulation deposited during use, thereby affecting the strength and noticeability of the fragrance and the effectiveness of the clothing wipe device described herein.

Manufacturing the clothing wipe device may be illustrated by a simple sequence of steps. Both the applicator and the pouch may be supplied in bulk as thin fabrics and packaging film respectively. Each one may be imprinted in bulk web-processing facilities prior to cutting and bonding the individual pieces that will be assembled to form the applicator or the pouch. Imprinting may be used to apply logo and other indicia, as well as instructions for use and/or attractive graphics, to the pouch. The fragrance mixture may also be applied during a bulk web-processing process by depositing the compound odor neutralizer material in a slot-dye coating process, well-known in the art. In this process, the formulated mixture is placed into a reservoir such as a hopper device and conveyed to a distributing device that has a narrow slot orifice oriented across the width of the fabric that is to receive the mixture. The slot has a length approximately equal to the width of the fabric, and deposits a measured layer of the odor neutralizer formulation onto the surface of the bottom, active (first) layer of the applicator.

Materials for the bottom (first) and top (second) layers of the applicator are selected for the abilities to be imprinted, bonded ultrasonically, and fabricated in a web-processing process as will be described. The bottom layer of the applicator may be a single ply of a non-woven (e.g., spun-bound) polypropylene fabric or a two-ply combination of a non-woven polypropylene fabric having a weight of approximately 160 g/m² weight and a rayon fabric that is needle punched in a predetermined pattern over the area of the layer to secure it to the polypropylene fabric. The total thickness of the two-ply layer may then have an approximate thickness of 0.10 inch or less. In a single layer embodiment the additional step to bond the rayon or other fabric layer may be deleted. The top layer of the applicator may preferably be a non-woven (e.g., spun-bound) polypropylene fabric of approximately 100 g/m² weight and a thickness of approximately 0.013 inch. These weights/thicknesses are approximate and selected for the size and weight appropriate to the look and feel of the hand-held clothing wipe device described in this example. Other materials may be selected as long as they have the properties suited to the application. For example, certain alternate embodiments intended for heavy-duty service may be fabricated of heavier weight materials or synthetic fabrics of greater durability.

In the embodiment of FIGS. 4-7, the two layers, after imprinting, depositing the odor neutralizer to the bottom layer and cutting to size, may be ultrasonically bonded around the perimeter except for along one edge, allowing the one edge to remain open, thereby forming a pocket so that the applicator may be slipped over a user's fingers during use. The bottom layer may preferably be provided in a color different from the top layer to facilitate identification of the correct side of the applicator to apply to the user's clothing. For example, the bottom layer may be white and the top layer imprinted with the logo, etc. in other colors. In another embodiment to be described with reference to FIGS. 8-10, two opposite edges of the applicator are left open—unbonded—thereby forming a sleeve for the user's fingers.

The storage pouch may be manufactured from a flexible packaging film that is imprinted with graphics, logos, legends, indicia, instructions for use, etc. As is well known, flexible packaging film is available in many forms depending on the kind of product to be contained therein and the kind of graphics imprinted on the outside layer, etc. In the illustrated example, the packaging film, which should be adapted to containing personal care products, may be a laminated product whereby each layer of the material is selected to provide the particular properties desired in the package. Such flexible packaging film products are typically laminated of multiple layers of thin film materials such as a coated and printable outer layer to support printed graphics (e.g., polyester), low density polyethylene (LDPE), a metal foil, a linear low density polyethylene film (LLDPEF), and the like. These materials may be provided in thicknesses that range from 0.25 to 1.5 mil (1 mil=1/1000 of an inch). In the embodiment described herein the total thickness of the film packaging material may be approximately 3.5 mil. These materials in combination provide sufficient body, moisture and puncture resistance, resistance to tearing, the effects of light, etc.

Figure 4:
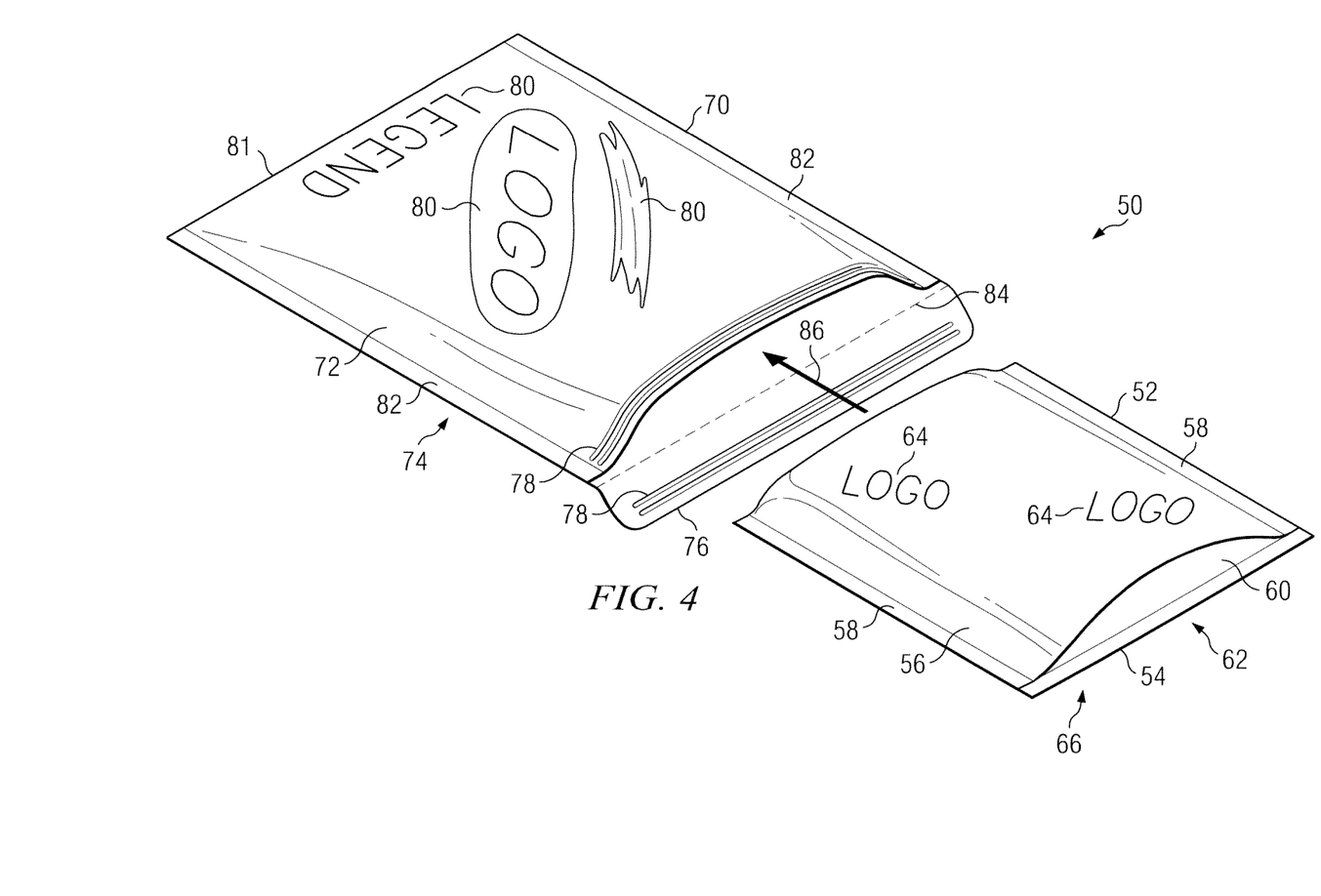
FIG. 4 illustrates a pictorial view of an alternate embodiment of an apparatus for neutralizing odors on a person's clothing.
Figure 7:
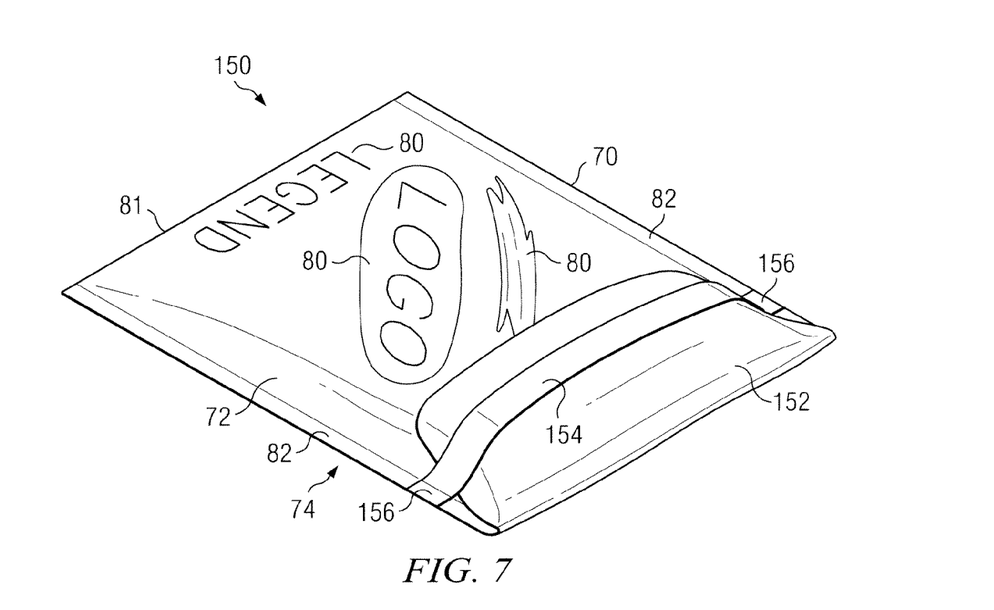
FIG. 7 illustrates an alternate embodiment of the applicator pouch shown in FIG. 4.

As shown in FIG. 4 the storage pouch 70 includes a closure mechanism along the one side or edge of the pouch that does not have a bound or welded edge along its perimeter. This open edge may be resealed to enclose the applicator therein when not in use so that the odor neutralizing capacity is preserved. One preferred closure mechanism is to provide the open edge with a string zipper—a flangeless zipper—or its equivalent. The locking members of the string zipper are sealed to the edges of the opening to be closed or opened. As is well-known, a string zipper allows for reclosing a package without requiring a separate traveling slider to zip or unzip the package. String zippers may be molded from polyethylene or other similar materials. Another closure mechanism is illustrated in FIG. 7. In this example the bottom layer of the applicator is extended past the opening along the edge of the applicator, thus forming a closure flap. A strap of the same material used for the top layer may be attached parallel to the open edge on the outside of the applicator and spaced slightly away from the open edge of the applicator to serve as a retainer for the closure flap.

FIG. 4 illustrates a pictorial view of an alternate embodiment of an apparatus for neutralizing odors on a person's clothing. This personal care product 50 includes an applicator 52 and a pouch 70. The applicator 52 is formed by bonding a bottom layer 54 of a suitable material to a top layer 56 of a suitable material along its edges 58 except for one edge 60 that is left open 62, thereby forming a pocket in the space between the top and bottom layers to enable a user to insert at least two fingers therein during use. Thus, in this embodiment, the first and second layers are bonded together along mutual edges thereof, except along a portion of the mutual edges—e.g., on one side or edge—thereby forming the pocket. The applicator 52 may be imprinted with graphics 64 such as brand name or logo indicia or other decorative features. The bottom layer 54 of the applicator 52 further includes an odor neutralizing formulation 66 applied-to or embedded or impregnated into the outer surface of the bottom layer 54. The formulation 66 is further described in FIG. 5.

Figure 6:
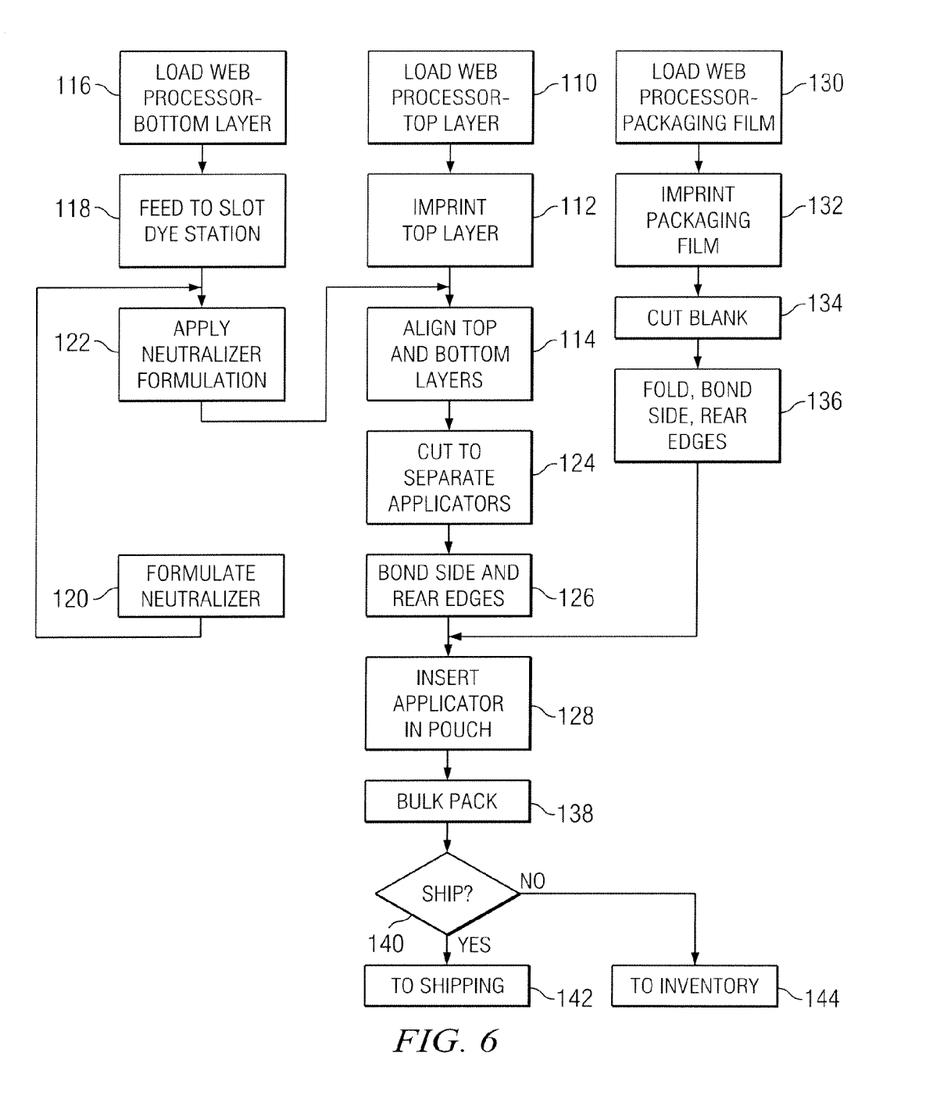
FIG. 6 illustrates a flow chart of one example of a method of manufacture of the embodiment of FIGS. 4 and 5.

Continuing with FIG. 4 a pouch 70 for storing the applicator 52 in when it is not in use is shown. The storage pouch 70 may be formed of a single sheet of flexible packaging film as described herein above, folded along an edge 81 and bonded along opposite side edges 82. The fabrication process is shown in FIG. 6 to be described. The pouch 70 includes a top side 72, a bottom side 74, and a closure flap 76 extending from the bottom side 74. The pouch 70 may also include graphics 80 such as decorative features, brand name, or logo indicia imprinted on the outer sides of the pouch. In the embodiment shown a string zipper 78 is provided as a first part on the underside of the closure flap 76 and a second part on the outer surface of the top side 72 of the pouch 70. The closure flap 76 may be folded along the dashed line 84 until the two parts of the string zipper 78 are placed in contact and pressed together. As is well-known, a string zipper is a reusable fastener for a package that includes complementary molded ridges that may be pressed together to seal the zipper. To open the package a user need only grasp the top and bottom sides along the string zipper 78 and pull the sides 72, 74 at their open edges apart to separate the ridges of the fastener.

Figure 5:
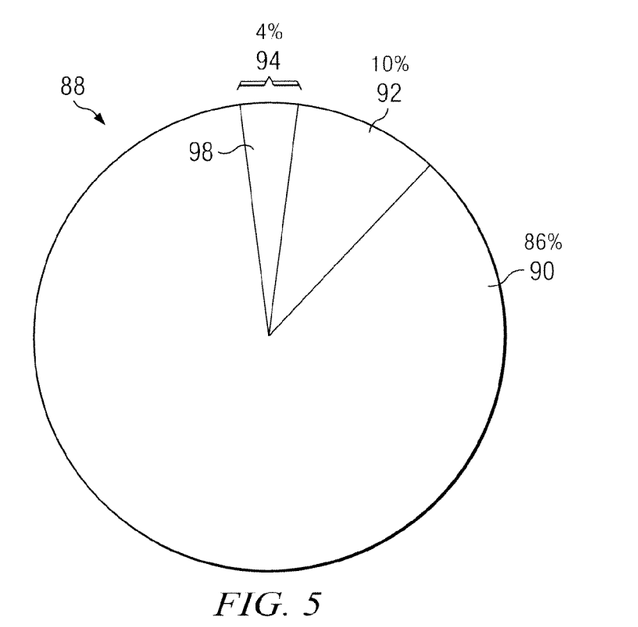
FIG. 5 illustrates a graphical depiction of an odor neutralizing formulation for use with the embodiment of FIG. 4.

FIG. 5 illustrates a graphical depiction of an odor neutralizing formulation 88 for use with the embodiment of FIG. 4. In FIG. 5, abuse component may be formed of a mixture of polyethylene glycol ester 90 (PEG ester) and glycerin 92, mixed together in approximate proportions (of the total odor neutralizing formulation) of 86% and 10% respectively. One example of the principal ingredient of a suitable base component is a product named: Mapeg® 6000 DS PEG (6000) Distearate, which is available from the BASF Corporation, Florham Park, N.J. 07932. This product is a polyethylene glycol ester widely used in soaps and other products as emulsifiers, stabilizers, viscosity control agents, and the like. There are variety of versions of this product available in various molecular weights and other parameters, etc. The glycerin 92 component is included to soften the PEG ester somewhat to enable smooth application of the odor formulation 88 on the user's clothing. Substitutes for the glycerin 92 may include other poly alcohols or long chain poly oils well-known in the art. The combination of the PEG ester 90 and the glycerin 92 enables slower, more uniform release of the fragrance mixture (to be described). The purpose of the base component 90, 92 is to provide a solid but soft carrier or delivery vehicle for the fragrance mixture that provides a barrier to the escape of bad odors ("malodors") from the fabric of the person's clothing or the person's hair. The base component provides a thin, transparent, colorless film upon the surface of the user's clothing, yet is washable and leaves no stain.

The odor neutralizer component 94 makes up the remaining 4% of the odor neutralizing formulation 88. One reason for the relatively small percentage—approximately 4%—used in the illustrated embodiment is that typically only a very small amount of a malodor substance is very noticeable. Accordingly, only a very small amount of a counteracting fragrance may be needed to be effective in neutralizing the malodor. Further, it is possible for a limited amount of a fragrance blend or composition to counteract a malodor or to neutralize an odor. For example, in an aroma compound based on an aldehyde, the aldehyde may react with nitrogen in a malodor to form what is known in the art as a "Schiff Base" product that "ties up" the nitrogen malodor materials, thereby reducing the perception of the malodor.

Continuing with FIG. 5, in the illustrated embodiment the odor neutralizer component 94 preferably includes a fragrance mixture 98 formulated from an essential oil in combination with at least one aroma compound to provide an odor characteristic that matches the desired odor paradigm. The aroma compound, such as the aldehydes, ketones, alcohols, or esters, as is well-known, react easily with the elements that are found in malodors—i.e., oxygen, nitrogen, and sulphur. A particular choice of aroma compound may be one of several that would be suitable for the type of clothing wipe 50 described herein. Thus, a preferred choice would be primarily a matter of (a) how the aroma compound reacts with other materials and (b) the desired subjective criteria associated with the scent of the aroma compound. As is well-known, an aroma compound typically may include many ingredients, combined in a proportion to yield a particular aroma or scent, in varying degrees of strength or intensity, duration of effects, etc., to name just a few kinds of characteristics.

In the present formulation these aroma compounds may include chemicals of an aromatic or aliphatic nature such as aldehydes, ketones, alcohols, esters, and/or materials containing oxygen, nitrogen or sulphur. One example of a fragrance mixture is perfume, which is a mixture of essential oils, aroma compounds, fixatives, and solvents, each selected to yield a desired particular effect. In the present invention, a fragrance mixture that presents a "clean linen" scent is preferred. However, there are many possible fragrance mixtures and fragrance paradigms that may be used in a device of the type described herein, including active scents (typically associated with masculine users) and floral scents (typically associated with feminine users) for example.

FIG. 6 illustrates a flow chart of one example of a method of manufacture of the embodiment of FIGS. 4 and 5. As is well-known, many products made from thin film or fabric materials may be suitably processed on web processing facilities. Web processing typically receives material from a bulk roll of material and may include mechanisms in various sequences for imprinting, coating, folding, bonding, depositing other substances thereon, cutting, filling, laminating, etc. Such processes are among those suitable for manufacturing both the applicator 50 and the pouch 70 described herein in FIG. 4. FIG. 6 depicts one such process applied to fabricate both the applicator 50 and the pouch 70. The method employs several web processing lines that begin with individual components of the clothing wipe, wherein the separate web processing lines or branches are merged in a single step to combine the individual processing lines or branches to join together two components of the finished product. This merging step may occur more than once, as illustrated in FIG. 6.

Continuing with FIG. 6, the flow for fabricating the applicator may begin at step 110 to load the web processor with the material for the top layer 56 of the applicator 52 followed by step 112 to imprint the top layer 56 with selected indicia or graphics 64 before sending the imprinted material to step 114. In a parallel process the material for the bottom layer 54 is loaded into a separate branch of a web processor in step 116 for forwarding via step 118 to feed the bottom layer 54 material through a machine such as used for a slot dye process to deposit measured amounts of the odor neutralizer formulation 66 onto the surface of the bottom layer 54. The odor neutralizer formulation 66 may be prepared in a step 120 and advanced to step 122 to be applied to the bottom layer 54 of the applicator 52.

As is well known, a slot dye process is adapted to dispense a measured amount of a substance from a narrow slot opening across the width of a moving belt of the film or fabric to be coated or imprinted. As readily understood by persons skilled in the art, alternatives to the slot dye process exist that also deposit a uniform coating of a material in fluid, powder, or granular form upon the surface of a fabric. The choice is best made to suit the particular form of the product being fabricated. The slot dye process is described as one readily understood method of applying a uniform coating of material to a surface of an object.

Figure 8:
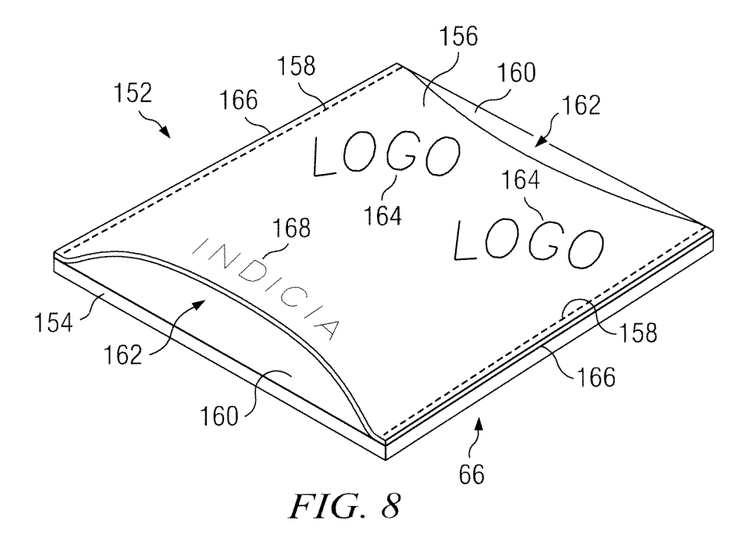
FIG. 8 illustrates a first alternate embodiment of the applicator.
Figure 9:
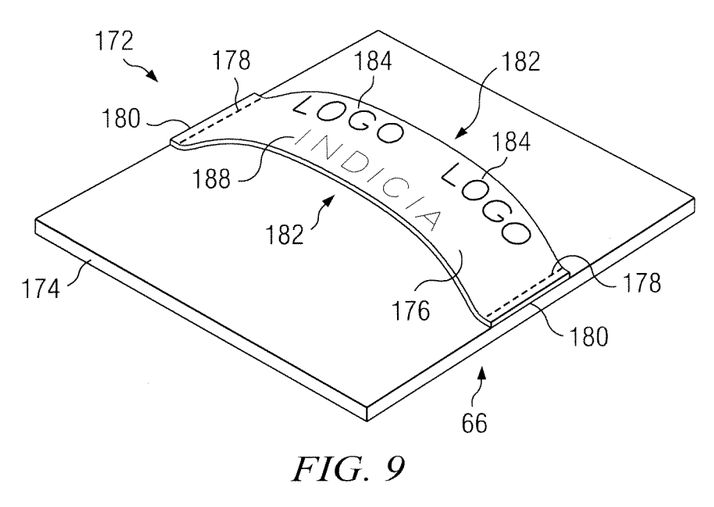
FIG. 9 illustrates a second alternate embodiment of the applicator.
Figure 10:
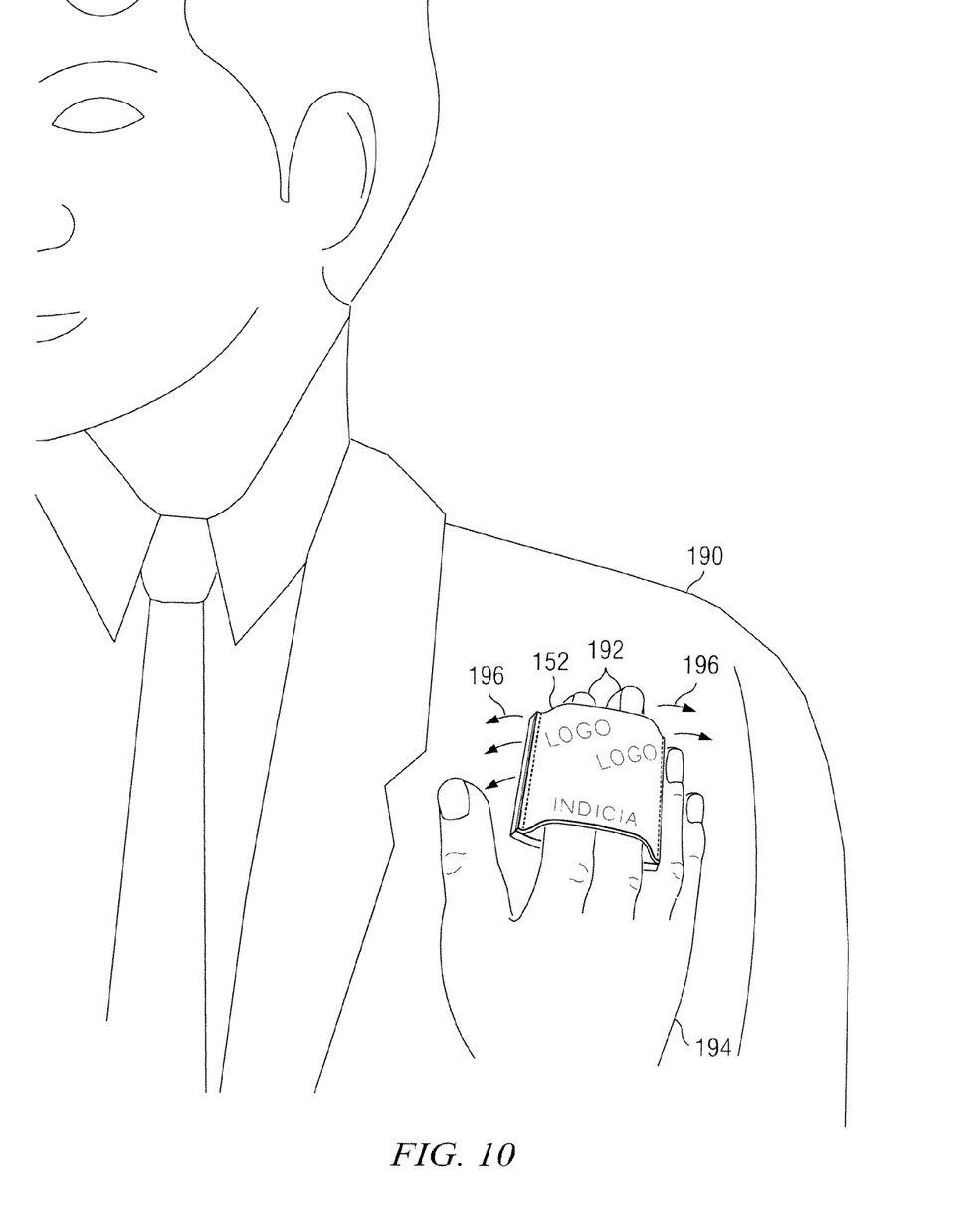
FIG. 10 illustrates a pictorial view of the use of the first or second alternate embodiments of the applicator.

Following deposit of the odor neutralizer formulation 66 the material for the bottom layer 54 is next prepared to be aligned with and joined to—i.e., merged with—the material for the top layer 56 in step 114. Following alignment, the flow advances to step 124 wherein the line of applicators formed to that point may be cut into separate applicators 52 followed by bonding the side and rear edges 58 of the aligned top 56 and bottom 54 layers together in step 126. Such bonding may utilize an ultrasonic bonding process to bond the edges of the top 56 and bottom 54 layers to each other, thereby forming an applicator 52 that may be worn as a small pouch or finger mitt as depicted in FIG. 3, or a sleeve as illustrated in FIGS. 8-10 that is slipped over the user's fingers. After the bonding step 126 the completed applicator 52 may be merged with the storage pouch 70 in step 128 and inserted into a storage pouch 70. The storage pouch 70 may be fabricated in a similar way to be described. In the bonding step, several alternative processes may be used including continuous ultrasonic, uniform discontinuous ultrasonic, and a stitched bond. The stitched bonding may be stitched with a thread material or be simulated by an intermittent (discontinuous) ultrasonic bonding.

Beginning at step 130 with loading the flexible packaging film for fabricating the pouch 70 the flow advances to step 132 to imprint the flexible packaging film with indicia such as product or brand name, logo, colorful graphics, instructions for use, other text to comply with regulatory requirements, etc. following imprinting, the imprinted film passes through a station to cut the blanks of the pouch 70 to size in step 134 before being folded, and the aligned side edges are bonded, again by an ultrasonic process, for example. The completed storage pouch 70 is aligned to merge with the completed applicator 52 in step 128, wherein the applicator 52 is inserted into the pouch 70, including folding over the flap 76 to seal it against the top layer 56 by pressing the two sides of the string zipper 78 together or otherwise securing the closure. The process may then deliver the finished clothing wipes 50 to a bulk packing station 138 to prepare them for shipment. Typically the clothing wipes manufactured as described may be packaged in quantities of one dozen to multiples of a dozen, for example. The packed products may proceed to a station 140 that tests whether the package is to be shipped immediately in step 142 according to an order or transferred to inventory in step 144. At this point, the flow ends.

As will be readily understood, the example of the fabrication process depicted in FIG. 6 is merely illustrative of one of several possible ways that the manufacture of these clothing wipe products may be accomplished. As noted herein above, the clothing wipe is a delivery vehicle well-suited to a wide variety of applications for delivering chemical-based products to the surface of a person's clothing or hair or skin. Its structure, regardless of the particular chemical formulations applied to the bottom layer of the clothing wipe, is thus basically the same as that described herein and adapted to being fabricated in the processes described and illustrated herein.

FIG. 7 illustrates an alternate embodiment 150 of the applicator storage pouch 70 shown in FIG. 4. As in FIG. 4, the pouch 70 may be formed of a single sheet of flexible packaging film as described herein above, folded along an edge 81 and bonded along opposite side edges 82. The basic fabrication process as shown and described in FIG. 6 may be used. The pouch includes a top side 72 and a bottom side 74, and may also include graphics 80 such as decorative features, brand name, or logo indicia imprinted on the outer sides of the pouch. In the embodiment of FIG. 7, a closure flap 152 extends from the bottom side 74. A retaining strap 154 for the flap 152 extends from each side edge 82 of the pouch where it is bonded to the respective side edge 82 at the locations 156 shown in FIG. 7. The flap 152 provides for closing and opening the pouch 70. Persons skilled in the art will realize that other closure methods or mechanisms are possible such as other types of zip fasteners, releasable adhesives and the like.

FIG. 8 illustrates a first alternate and preferred embodiment of the applicator. In this embodiment of the applicator 152, both ends of the applicator 152 are open, thereby forming a sleeve to permit the user's fingertips to extend beyond the end of the applicator. Further, the bonding of the bottom 154 and top 156 layers on either side edges 166 of the applicator 152 is indicated by the dashed lines 158. Indicia 168 are shown on the top layer 156. The same materials are used in the fabrication of this embodiment as the embodiment of FIG. 4 but the structure is slightly different, reflecting improved utility and only one of several other possible variations.

Continuing with FIG. 8, the applicator 152 is formed by bonding a bottom layer 154 of a suitable material to a top layer 156 of a suitable material along first and second side edges 166, leaving both ends 160 open—i.e., forming a sleeve by providing a passage between the first and second layers—to enable a user to insert at least two fingers in and through the space or passage 162 between the layers 154, 156 of the applicator 152 during use. The feature of permitting the user's fingers to extend through the passage or sleeve 162 of the applicator 152 has been found to work well because the applicator 152 is less likely to slip off the user's finger during its use. The bonding of the top 156 and bottom 154 layers is indicated by the dashed lines 158 along the side edges 166 of the applicator 152. The dashed lines 158 may indicate the location of ultrasonic bonds or, alternatively, the stitches of a sewn binding. The applicator 152 may be imprinted with graphics 164 such as brand name or logo, or indicia 168 or other decorative features. The bottom layer 154 of the applicator 152 further includes an odor neutralizing formulation 66 embedded, impregnated, or otherwise applied into or upon the outer surface of the bottom layer 154. The odor neutralizing formulation 66 is further described in FIG. 5.

FIG. 9 illustrates a second alternate embodiment of the applicator. In this embodiment of the applicator 172, both ends of the applicator 172 are open to permit the user's fingertips to extend through the space 182 between the bottom 174 and top 176 layers of the applicator 172. In this embodiment the top layer 176 is formed as a strap across the midsection of the applicator 172. The bonding of the bottom 174 and top 176 layers on either side of the applicator 172 is indicated by the dashed lines 178, and indicia 188 are shown on the upper layer 176. This embodiment of the applicator 172 is a variation of the embodiment depicted in FIG. 8 that may be implemented to save cost, for example. The same materials are used in its fabrication but the structure is slightly different, reflecting one of several possible variations.

Continuing with FIG. 9, The applicator 172 is formed by bonding a bottom layer 174 of a suitable material to a top layer 176 or strap of a suitable material along both side edges 180, leaving both ends of the applicator 172 open to enable a user to insert at least two fingers in and through the space 182 of the applicator 172 during use. The feature of permitting the user's fingers to extend through the space 182 of the applicator 172 in the manner of a sleeve has been found to work better because the applicator 172 is less likely to slip off the user's finger during its use. The bonding of the top 176 and bottom 174 layers is indicated by the dashed lines 178 along the side edges 180 of the applicator 172. The dashed lines 178 may indicate the location of ultrasonic bonds or, alternatively, the stitches of a sewn binding. The applicator 172 may be imprinted with graphics 184 such as brand name or logo, or indicia 188 or other decorative features. The bottom layer 174 of the applicator 172 further includes an odor neutralizing formulation 66 embedded or impregnated into or otherwise applied upon the outer surface of the bottom layer 174. The odor neutralizing formulation 66 is further described in FIG. 5.

FIG. 10 illustrates a pictorial view of the use of the first or second alternate embodiments of the applicator. This view is similar to FIG. 3 except the user is shown with the embodiment of FIG. 8 in use. The use of the embodiment of FIG. 9 is similar. The applicator 152 is shown being manipulated by a wiping action against the clothing 190 of a user, as indicated by the arrows 196. The user's fingertips 192 of his or her hand 194 are inserted into the space or sleeve 162 between the bottom 154 and top 156 layers of the applicator 152. In a preferred embodiment, the space 162 in the applicator 152, when opposite sides 166 (See FIG. 8) of the applicator 152 are squeezed slightly, opens wide enough to receive two fingertips 192 therein for manipulating the applicator 152. Once installed on the user's fingertips, his or her hand 194 is moved in a side-to-side motion 196, rubbing or wiping the lower surface portion (not visible in the figure, but will be readily understood) of the bottom layer 154 against the surface of the clothing 190. This action causes the release and transfer of the odor neutralizing formulation 66 (See FIG. 5) from a portion of the bottom layer 154 to the surface of the user's clothing 190. An important attribute of the applicator 152 (and also other embodiments thereof as described herein) is that it enables a controlled release of the amount and strength of the fragrance component upon the user's clothing or hair when rubbed against these surfaces.

The applicators 10, including embodiments 52, 152, 172, and variations thereof, described herein above may be used multiple times and stored in a person's pocket or purse when not in use. However, in an alternate embodiment, the applicator 10 may be enclosed in a protective wrapper (See, e.g., FIG. 4) that is removed by the user prior to use. This wrapper or pouch may be configured to retard deterioration or prevent inadvertent dispersion of the odor neutralizing formulation or odor masking substances that may occur between uses. In another alternate embodiment, a protective layer of thin paper or plastic material having a low tack adhesive may be attached as a fourth layer (not shown) to the underside of the carrier layer 26. To activate the carrier layer 26, the user need only remove the fourth layer for use and replace the fourth protective layer over the carrier layer 26 after use. In a variation of this alternate embodiment, microcapsules of the odor neutralizing substance may be embedded in the adhesive that secures the protective layer to the carrier layer. Such microcapsules are well-known in the art for incorporating sample fragrances in periodical advertisements for the fragrance products. The microcapsules are ruptured when the protective layer is peeled away from the carrier layer, thus releasing or activating the odor neutralizing substance just prior to the use of the applicator 10. In another variation the fragrance mixture may be encapsulated in a starch compound, for example. Encapsulates act to retard the volatility of the fragrance mixture until it is released by contact or other action to open the encapsulate. Other mechanisms are spray dry fragrances, which can be deposited on clothing and released with friction against the fabric.

While the invention has been shown in only one of its forms, it is not thus limited but is susceptible to various changes and modifications without departing from the spirit thereof. For example, the embodiment illustrated in the drawings is shown with the opening disposed in one of the longer sides of the applicator 10. In one modification (not shown because its appearance is readily visualized to one skilled in the art, based on the structural features shown in FIGS. 1, 2 and 3), the opening for receiving the user's fingertips may be provided in one of the shorter sides of the applicator, thus permitting insertion of the user's fingers to a greater extent to provide a firmer grip on the applicator 10.

In another modification, the applicator 10 may be enlarged such that a user's entire hand fits within the pocket 28 between the substrate 24 and carrier 26 layers. This configuration enables the use of the applicator as a hand mitt, for applying odor neutralizing substances to a larger fabric surface area, for example, such as to upholstery in vehicles or on furniture or draperies and curtains in offices or residences, etc.

As noted herein above, potential market segments for clothing wipes as described herein may be gender-specific or unisex, or directed to particular kinds of activities such as indoor or outdoor, social or business or recreation, etc. Other applications may include clothing wipes that are formulated as insect repellants or other ancillary uses besides refreshing the scent or odors present on a person's clothing or hair. Other applications may include wipes having formulations adapted to a person's skin surfaces. Such applications may include ingredient formulations based on other types of ingredients in other proportions, etc. Thus, the clothing wipe described herein is only one example of a versatile delivery system for scented or other chemical formulations configured for a wide variety of personal care products.

Yet another modification is to provide a pouch or sleeve 70 as described in FIG. 4 for enclosing and storing the applicator 10 within when not in use. Such a pouch or sleeve may also protect the carrier layer 26 from contact with other surfaces or substances that could degrade its functional characteristics. A sleeve could also be employed as part of a mechanism for activating the applicator just prior to use, if that is a particular objective of the product. In this embodiment, removing the applicator 10 from enclosure or contact with the sleeve may serve to activate the odor neutralizing substance for use.

What is claimed is:
1. A personal care apparatus for neutralizing odors on clothing, comprising:
   a hand-held applicator formed of a first layer and a second layer bonded together along first and second opposite sides thereof to form a finger space therebetween; and
   an odor neutralizing formulation uniformly deposited on an outer side of said first layer of said applicator and comprising a solid matrix combining:

a base component comprising a mixture of 80% to 90% polyethylene glycol and 6% to 16% glycerin of said formulation; and a neutralizer component formulated from at least one essential oil in combination with an aroma compound and comprising 0.5% to 10% of said formulation.

2. The apparatus of claim 1, further comprising:

a pouch for enclosing said applicator when not in use.

3. The apparatus of claim 2, wherein said pouch comprises:

a pouch formed of a packaging film and having a reusable closure mechanism disposed along one side thereof.

4. The apparatus of claim 3, wherein said reusable closure mechanism of said pouch is selected from the group consisting of a string zipper, a tongue-and-loop closure, and a closure flap.

5. The apparatus of claim 1, further comprising:

a pouch formed of a packaging film for sealably enclosing said applicator and having a reusable string zipper closure mechanism along one side thereof.

6. The apparatus of claim 1, wherein said finger space of said applicator comprises:

a sleeve large enough to receive at least two adjacent fingers of a users hand therein.

7. The apparatus of claim 1, wherein said first layer of said applicator comprises:

a non-woven polypropylene fabric of approximately 160 g/m² weight.

8. The apparatus of claim 1, wherein said second layer of said applicator comprises:

a non-woven polypropylene fabric of approximately 100 g/m² weight.

9. The apparatus of claim 1, wherein said first and second opposite sides of the applicator are sonically bonded together.

10. The apparatus of claim 1, wherein said base component comprises:

a mixture of a polyethylene glycol and glycerin in approximate respective percentages of 86% and 10%.

11. The apparatus of claim 1, wherein said neutralizer component comprises:

a fragrance mixture blended from constituents selected from the group consisting of aldehydes, ketones, alcohols, esters, and materials containing oxygen, nitrogen, or sulphur.

12. The apparatus of claim 11, wherein said fragrance mixture comprises:

a compound selected from the group consisting of a masking agent, a solvent, an absorbant, an encapsulate, and a spray dry fragrance.

13. The apparatus of claim 11, wherein said fragrance mixture is formulated from an essential oil in combination with an aroma compound to provide a scent characteristic of clean linen.

14. The apparatus of claim 13, wherein said aroma compound comprises:

a mixture of ingredients selected from the group consisting of an aldehyde, a ketone, an alcohol, an ester, an oxygen-containing material, a nitrogen-containing material, and a sulphur-containing material.

15. The apparatus of claim 1, wherein said neutralizer component comprises:

approximately 4% of said odor neutralizing formulation.

16. The apparatus of claim 1, wherein said odor neutralizing formulation comprises:

a base component comprising a solid but soft mixture of 80% to 90% polyethylene glycol and 6% to 16% glycerin of said formulation; and a neutralizer component comprising a selected fragrance mixture formulated from the at least one essential oil in combination with an aroma compound to provide a scent characteristic of clean linen.

17. The apparatus of claim 16, wherein said fragrance mixture includes:

a compound selected from the group consisting of a masking agent, a solvent, an absorbant, an encapsulate, and a spray dry fragrance.

18. The apparatus of claim 16, wherein said aroma compound comprises:

a mixture of ingredients selected from the group consisting of an aldehyde, a ketone, an alcohol, an ester, an oxygen-containing material, a nitrogen-containing material, and a sulphur-containing material.

19. The apparatus of claim 1, wherein said first and second layers are bonded together along mutual edges thereof except along a portion of said mutual edges thereby forming a pocket between said layers.

20. The apparatus of claim 1, wherein said second layer is formed as a strap disposed across a mid-section of said applicator between said first and second opposite sides thereof.

21. The apparatus of claim 1, adapted to delivering an insect repellant substance to the surface of a person's clothing, wherein said odor neutralizing formulation includes an insect repellant chemical.

\* \* \* \* \*